(12) United States Patent
Matsumoto

(10) Patent No.: US 9,740,166 B2
(45) Date of Patent: Aug. 22, 2017

(54) FLUORESCENCE RECEIVING APPARATUS AND FLUORESCENCE RECEIVING METHOD

(71) Applicant: HAMAMATSU PHOTONICS K.K., Hamamatsu-shi, Shizuoka (JP)

(72) Inventor: Naoya Matsumoto, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 14/772,570

(22) PCT Filed: Mar. 4, 2014

(86) PCT No.: PCT/JP2014/055491
§ 371 (c)(1),
(2) Date: Sep. 3, 2015

(87) PCT Pub. No.: WO2014/136784
PCT Pub. Date: Sep. 12, 2014

(65) Prior Publication Data
US 2016/0018786 A1 Jan. 21, 2016

(30) Foreign Application Priority Data
Mar. 6, 2013 (JP) .................................. 2013-044348

(51) Int. Cl.
*G03H 1/08* (2006.01)
*G03H 1/12* (2006.01)
(Continued)

(52) U.S. Cl.
CPC ....... *G03H 1/0005* (2013.01); *G01N 21/6456* (2013.01); *G01N 21/6458* (2013.01);
(Continued)

(58) Field of Classification Search
CPC ...... G03H 1/08; G03H 1/0808; G03H 1/0841; G03H 2001/0816; G03H 2001/0825;
(Continued)

(56) References Cited

U.S. PATENT DOCUMENTS

2010/0142014 A1* 6/2010 Rosen .................... G03B 35/02 359/1
2011/0267663 A1 11/2011 Murayama

FOREIGN PATENT DOCUMENTS

CN 101632134 1/2010
CN 101680749 3/2010
(Continued)

OTHER PUBLICATIONS

English-language translation of International Preliminary Report on Patentability (IPRP) dated Sep. 17, 2015 that issued in WO Patent Application No. PCT/JP2014/055491.
(Continued)

Primary Examiner — Jade R Chwasz
(74) Attorney, Agent, or Firm — Drinker Biddle & Reath LLP

(57) ABSTRACT

A fluorescence receiving apparatus comprises an excitation light source, a spatial light modulator of a phase modulation type for phase-modulating excitation light to obtain phase-modulated light, a focusing optical system configured to focus the phase-modulated light to a specimen, a specimen stage for supporting the specimen, a fluorescence receiver for receiving fluorescence generated by focus of the phase-modulated light to the specimen, a control unit for displaying a first CGH on the spatial light modulator, and a correction unit for correcting the first CGH. The correction unit comprises a receiver-specific sensitivity information storage preliminarily acquiring and storing sensitivity information per reception position specific to the fluorescence receiver, and a second hologram generator for correcting the
(Continued)

first CGH, based on intensities of the fluorescence and the sensitivity information, to generate a second CGH. The control unit displays the second CGH on the spatial light modulator.

8 Claims, 9 Drawing Sheets

(51) Int. Cl.
- *G03H 1/00* (2006.01)
- *G01N 21/64* (2006.01)
- *G02B 21/16* (2006.01)
- *G03H 1/22* (2006.01)
- *G02B 21/00* (2006.01)

(52) U.S. Cl.
CPC ....... *G02B 21/008* (2013.01); *G02B 21/0032* (2013.01); *G02B 21/0076* (2013.01); *G02B 21/16* (2013.01); *G03H 1/0808* (2013.01); *G03H 1/2294* (2013.01); *G03H 2001/005* (2013.01); *G03H 2001/0825* (2013.01)

(58) Field of Classification Search
CPC ..... G03H 2001/0833; G03H 2001/085; G03H 2001/0858; G03H 2210/40; G03H 2210/44; G03H 2210/441; G03H 2210/45; G03H 1/10; G03H 1/12; G03H 1/14; G03H 1/264; G03H 2001/266; G03H 2001/2665; G03H 2001/267; G03H 2001/2675; G03H 2001/0489; G03H 2210/10; G03H 2210/20; G03H 2210/30; G03H 2225/33; G03H 2225/34; G03H 1/0005; G03H 2001/0077; G03H 2001/0439; G03H 1/24; G03H 2001/0212; G03H 2222/14; G03H 2222/15; G03H 2222/16; G03H 2222/17; G03H 2222/18; G03H 2222/20; G03H 2222/23; G03H 2222/24; G03H 2222/31; G03H 2222/32; G03H 2222/33; G03H 2222/34; G03H 2222/35; G03H 2222/36; G03H 1/2294; G02B 26/106; G02B 21/06; G02B 21/16; G02B 21/00; G02B 21/0032; G02B 21/0056; G02B 21/0076; G02B 21/008; G02B 21/26; G02B 21/361; G02B 21/365; G01N 21/6456; G01N 21/6458
USPC .................. 359/9, 10, 11, 15, 16, 22, 27, 31
See application file for complete search history.

(56) References Cited

FOREIGN PATENT DOCUMENTS

| | | |
|---|---|---|
| EP | 0 840 159 | 5/1998 |
| JP | H10-186283 A | 7/1998 |
| JP | 2005-292662 A | 10/2005 |
| JP | 2009-103958 A | 5/2009 |
| JP | 2009-300589 A | 12/2009 |
| JP | 4531431 | 8/2010 |
| JP | 2011-128572 A | 6/2011 |
| WO | WO-2004/017069 A1 | 2/2004 |

OTHER PUBLICATIONS

Volodymyr Nikolenko et al., "SLM microscopy: scanless two-photon imaging and photostimulation with spatial light modulators," Frontiers in Neural Circuits, Dec. 19, 2008, pp. 1-14, vol. 2, article 5.

Yonghong Shao et al., "Ultrafast, large-field multiphoton microscopy based on an acoustooptic deflector and a spatial light modulator," Optics Letters, Jul. 1, 2012, pp. 2532-2534, vol. 37, No. 13.

Liang Yan-ming et al., "Reconstruction and Visualization of Multiplane Images Based on Spatial Light Modulator", State Key Laboratory of Optoelectronic Materials and Technologies, Sun Yat-sen University, Guangzhou 510275, China, vol. 39 No. 10 , Oct. 2010, p. 1820-p. 1824, including English-language Abstract.

\* cited by examiner (a)

(b)

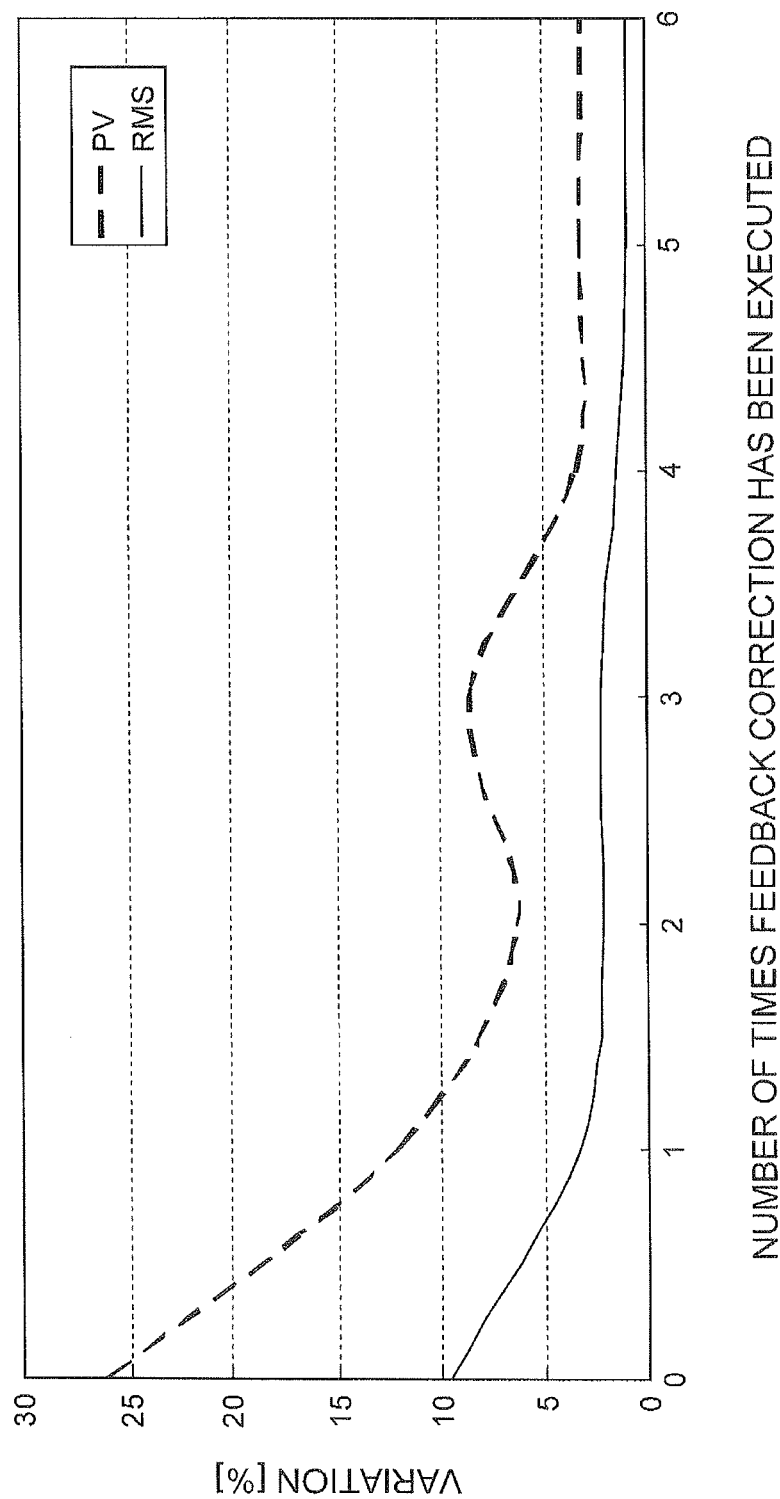

FLUORESCENCE RECEIVING APPARATUS AND FLUORESCENCE RECEIVING METHOD

TECHNICAL FIELD

The present invention relates to a fluorescence receiving apparatus and a fluorescence receiving method.

BACKGROUND ART

There is a conventionally-known fluorescence scanning microscope for generating a plurality of light spots on a specimen with use of an acousto-optic modulation element which is one of spatial light modulators (Spatial Light Modulator, which will be referred to hereinafter as "SLM") (e.g., cf. Patent Literature 1 and Non Patent Literature 1). For example, according to the disclosure of Patent Literature 1, the fluorescence scanning microscope has the effects of permitting free change in the number, positions, intervals, or the like of scan points to be simultaneously scanned, without loss of light quantity, reducing an image acquisition time, and permitting flexible observation according to usage.

CITATION LIST

Patent Literature

Patent Literature 1: Japanese Patent Application Laid-open Publication No. 2009-103958

Non Patent Literature

Non Patent Literature 1: Yonghong Shao et al., "Ultrafast, large-field multiphoton microscopy based on an acousto-optic deflector and a spatial light modulator," OPTICS LETTERS, Vol. 37, No. 13, July 2012.

SUMMARY OF INVENTION

Technical Problem

When the SLM is introduced into an optical system of the fluorescence scanning microscope and a pattern indicative of a phase distribution or an intensity distribution called a CGH (Computer Generated Hologram) is presented on the SLM, multiple spots can be generated on focusing points of an objective lens. For this reason, fluorescence excited from a specimen also forms a plurality of spots. When this is received by a multi-anode photomultiplier tube or the like, multi-spot measurement becomes feasible. However, a major problem is control of intensities of the multiple spots of light at the focusing positions. This is attributed to the fact that there is variation in the multiple spots generated on the SLM and there is also sensitivity variation in the multi-anode photomultiplier tube or the like on the observation side. On the other hand, neither of the foregoing Patent Literature 1 and Non Patent Literature 1 mentions or suggests the control of intensities of the multiple spots of light at the focusing positions.

Therefore, the present invention has been accomplished in view of the above-described circumstances and it is an object of the present invention to provide a fluorescence receiving apparatus and a fluorescence receiving method enabling the control of the intensities of the multiple spots of light at the focusing positions.

Solution to Problem

In order to solve the above problem, a fluorescence receiving apparatus (fluorescence detecting apparatus) according to one aspect of the present invention is an apparatus for detecting fluorescence generated by excitation light modulated by a spatial light modulator, which comprises: an excitation light source for outputting the excitation light; the spatial light modulator to which the excitation light is input, which expresses (or presents) a first hologram, thereby to modulate at least either one of a phase and an amplitude of the excitation light, and which outputs modulated light; a focusing optical system provided as a subsequent stage to the spatial light modulator and configured to focus the modulated light to a specimen; a specimen stage on which the specimen is mounted; a fluorescence detector for detecting fluorescence generated by focus of the modulated light to the specimen, via the focusing optical system; a control unit for making the spatial light modulator express (or present) the first hologram, thereby to modulate at least either one of the phase and the amplitude of the excitation light at each of a plurality of two-dimensionally arrayed pixels, and for making the focusing optical system focus the modulated light at focusing positions of the specimen; and a correction unit for correcting the first hologram, wherein the correction unit corrects the first hologram, based on sensitivity information per reception position specific to the fluorescence detector and intensities of the fluorescence at the focusing positions, to generate a second hologram, and wherein the control unit controls the spatial light modulator so as to express (or present) the second hologram.

A fluorescence receiving method (fluorescence detecting method) according to one aspect of the present invention is a method for receiving (or detecting) fluorescence generated by excitation light modulated by a spatial light modulator, wherein the excitation light output from an excitation light source is input to the spatial light modulator, wherein the spatial light modulator is made to express (or present) a first hologram, thereby to output modulated light obtained by modulating at least either one of a phase and an amplitude of the excitation light, wherein a focusing optical system provided as a subsequent stage to the spatial light modulator is made to focus the modulated light to a specimen, wherein a fluorescence detector is made to detect fluorescence generated by focus of the modulated light to the specimen, via the focusing optical system, wherein the first hologram is corrected based on sensitivity information per reception position specific to the fluorescence detector and intensities of the fluorescence at focusing positions, to generate a second hologram, and wherein the spatial light modulator is made to express (or present) the second hologram, thereby to output modulated light obtained by modulating at least either one of the phase and the amplitude of the excitation light.

According to the fluorescence receiving apparatus and fluorescence receiving method according to one aspect of the present invention as described above, the first hologram first presented on the spatial light modulator by the control unit is corrected by the correction unit and the second hologram newly generated by the correction is again presented on the spatial light modulator by the control unit. Namely, the hologram is fed back by the correction unit and the control unit, so as to perform the correction of the hologram. The second hologram is obtained by the correction of the first hologram, based on the intensities of the fluorescence at the focusing positions and the sensitivity information per reception position specific to the fluorescence receiver, and this second hologram is used to control the intensity variation at the multiple spots generated by the spatial light modulator, for example, to a uniform intensity level, with consideration of the sensitivity variation in the fluorescence receiver. By the feedback correction of the hologram herein, each of the phase-modulated light applied to the specimen and the fluorescence emitted from the specimen is controlled, for example, to a uniform intensity level. Particularly, since the correction by the correction unit is performed based on the sensitivity information per reception position specific to the fluorescence receiver, location-dependent sensitivity variation per reception position specific to the fluorescence receiver is admitted but influence of the sensitivity variation can be reduced.

In the fluorescence receiving apparatus and fluorescence receiving method according to one aspect of the present invention, the correction by the correction unit may be performed for each of the plurality of focusing positions.

According to the fluorescence receiving apparatus and fluorescence receiving method according to one aspect of the present invention, the correction by the correction unit is performed for each of the plurality of focusing positions and, for this reason, the correction can be applied to each of the multiple spots generated by the spatial light modulator and the hologram.

In the fluorescence receiving apparatus and fluorescence receiving method according to one aspect of the present invention, the excitation light source may be a short pulsed laser capable of inducing multiphoton excitation.

The fluorescence receiving apparatus and fluorescence receiving method according to one aspect of the present invention are particularly useful to variation of intensities at the plurality of focusing positions, which prominently occurs in use of the short pulsed laser capable of inducing multiphoton excitation.

In the fluorescence receiving apparatus and fluorescence receiving method according to one aspect of the present invention, the fluorescence detector may be a multi-anode type photomultiplier tube.

The fluorescence receiving apparatus and fluorescence receiving method according to one aspect of the present invention are particularly useful to the fluorescence receiver with location-dependent sensitivity variation, such as the multi-anode type photomultiplier tube.

In the fluorescence receiving apparatus and fluorescence receiving method according to one aspect of the present invention, the specimen may be comprised of a homogeneous fluorescent material without location-dependent variation in a ratio of intensities of the fluorescence generated from the specimen to the modulated light focused to the specimen.

When the homogeneous fluorescent material without location-dependent variation is used as the specimen in controlling both of the modulated light to the specimen and the fluorescence from the specimen, for example, to uniform intensity levels, computational complexity can be reduced and the control can be readily and suitably performed.

In the fluorescence receiving apparatus and fluorescence receiving method according to one aspect of the present invention, the correction by the correction unit may be performed for each of scanned layers at predetermined intervals along an optical-axis direction of an objective lens included in the focusing optical system.

This also allows the fluorescence receiving apparatus and fluorescence receiving method according to one aspect of the present invention to be applied to the specimen with some depth.

In the fluorescence receiving apparatus and fluorescence receiving method according to one aspect of the present invention, scanning for each of the scanned layers may be performed in such a manner that the spatial light modulator controls the focusing positions in the optical-axis direction of the objective lens.

This allows the scanning for each of the scanned layers to be suitably performed.

Advantageous Effect of Invention

The present invention can provide the fluorescence receiving apparatus and fluorescence receiving method enabling the control of the intensities of the multiple spots of light at the focusing positions.

BRIEF DESCRIPTION OF DRAWINGS

FIG. 9 is a thawing showing a relationship between the number of times the feedback correction has been executed according to the embodiment of the invention (horizontal axis) and variation of fluorescence intensities (vertical axis).

LIST OF REFERENCE SIGNS 1 fluorescence receiving apparatus; 10 excitation light source; 11 spatial filter; 12 collimating lens; 13 mirror; 20 spatial light modulator; 21 control unit; 22 correction unit; 221 first hologram input unit; 222 receiver-specific sensitivity information storage; 223 second hologram generator; 30 focusing optical unit; 31 bi-telecentric lens system; 32 dichroic mirror; 33 objective lens; 34 lens; 90 specimen; 91 focusing positions; 92 specimen stage; L1 excitation light; L2 phase-modulated light; L3 fluorescence.

DESCRIPTION OF EMBODIMENTS

An embodiment of the fluorescence receiving apparatus and fluorescence receiving method according to the present invention will be described below in detail with reference to the accompanying drawings. In the description of the drawings the same elements will be denoted by the same reference signs, without redundant description.

(Configuration of Fluorescence Receiving Apparatus 1)

Figure 1:
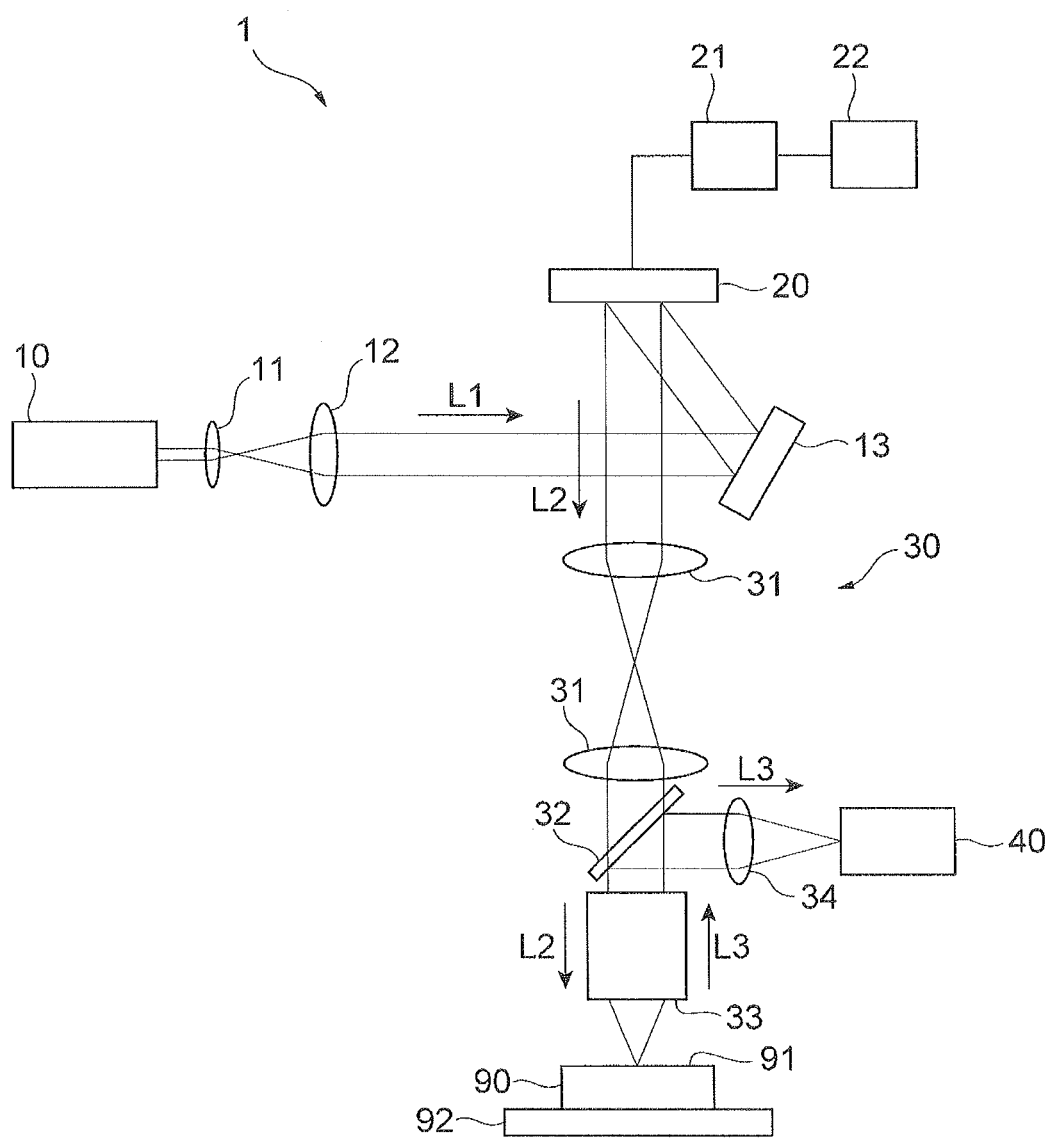
FIG. 1 is a drawing showing a general configuration of fluorescence receiving apparatus 1.

First, an overall configuration of fluorescence receiving apparatus (fluorescence detecting apparatus) 1 according to the present embodiment will be described. FIG. 1 is a drawing showing the general configuration of the fluorescence receiving apparatus 1. The fluorescence receiving apparatus 1 shown in this figure is an apparatus for detecting fluorescence L3 generated from a specimen 90 by modulation of excitation light L1 and focus of modulated light L2, which is configured with an excitation light source 10, a spatial filter 11, a collimating lens 12, a mirror 13, a spatial light modulator 20, a control unit 21, a correction unit 22, a focusing optical system 30, and a fluorescence receiver (fluorescence detector) 40; e.g., it is a fluorescence scanning microscope apparatus, STED microscope apparatus, PALM, STORM, or the like.

The excitation light source 10 is a light source that outputs the excitation light L1 to be applied to focusing positions 91 of the specimen 90. The excitation light source 10 may output a laser beam as excitation light L1 and may be, for example, a pulsed laser light source such as a femtosecond laser light source or an Nd:YAG laser light source. The excitation light source 10, which does not have to be limited to the foregoing examples, may be any one of an LD (Laser Diode), an SLD (Super Luminescent Diode), a halogen lamp, a xenon lamp, and so on. The excitation light L1 output from the excitation light source 10 travels through the spatial filter 11, is collimated by the collimating lens 12, and is reflected by the mirror 13 to impinge on the spatial light modulator 20. Without having to be limited to this configuration, the apparatus may be equipped with an expander lens (not shown), instead of the combination of the spatial filter 11 and the collimating lens 12. In this case, the excitation light L1 from the excitation light source 10 is expanded by the expander lens and is reflected by the mirror 13 to impinge on the spatial light modulator 20.

The spatial light modulator 20 is of a phase modulation type and is configured to input the excitation light L1 and output the phase-modulated light L2 resulting from phase modulation of the excitation light L1. Namely, the spatial light modulator 20 inputs the excitation light L1 output from the excitation light source 10, implements the phase modulation of the excitation light L1 with use of a hologram to modulate the phase of the excitation light L1 at each of a plurality of two-dimensionally arrayed pixels, and outputs the phase-modulated light L2 after the phase modulation. The hologram used in this spatial light modulator 20 may be a hologram obtained by numerical computation (Computer Generated Hologram, which will be referred to hereinafter as "CGH").

This spatial light modulator 20 may be of a reflection type or may be of a transmission type. The spatial light modulator 20 of the reflection type to be used herein may be any one of a LCOS (Liquid Crystal on Silicon) type, a MEMS (Micro Electro Mechanical Systems) type, and an optical address type. The spatial light modulator 20 of the transmission type to be used herein may be an LCD (Liquid Crystal Display) type, or the like. Furthermore, without having to be limited to the foregoing examples, the spatial light modulator to be used herein may be of a Segment Mirror type or a Continuous Deformable Mirror type.

The spatial light modulator 20 may be of an amplitude (intensity) modulation type, which is configured to input the excitation light L1 and output the modulated light L2 obtained by amplitude modulation of the excitation light L1. Namely, the spatial light modulator 20 inputs the excitation light L1 output from the excitation light source 10, implements the amplitude modulation of the excitation light L1 with use of a hologram to modulate the amplitude of the excitation light L1 at each of a plurality of two-dimensionally arrayed pixels, and outputs the amplitude-modulated light L2 after the amplitude modulation. The spatial light modulator 20 of the amplitude (intensity) modulation type may be of a reflection type or a transmission type and examples thereof include the MEMS (MicroElectro Mechanical Systems) type including DLP of Texas Instruments, Inc. and LCD (Liquid Crystal Display) type spatial light modulators. The hologram to be used in this spatial light modulator 20 may be a hologram obtained by numerical computation (Computer Generated Hologram, "CGH" hereinafter). In FIG. 1, the spatial light modulator 20 exemplified is the spatial light modulator of the reflection type and the phase modulation type and the description hereinbelow will concern the case using the spatial light modulator of the phase modulation type.

The control unit 21 is a unit that makes the spatial light modulator 20 express the CGH, thereby to modulate the excitation light L1 at each of the two-dimensionally arrayed pixels and that makes the focusing optical system 30 focus the modulated light L2 at a plurality of focusing positions 91 of the specimen 90. For example, when the spatial light modulator 20 is the spatial light modulator of the phase modulation type, the control unit 21 makes the spatial light modulator 20 present the CGH to modulate the phase of the excitation light L1 at each of the two-dimensionally arrayed pixels, and makes the focusing optical system 30 focus the phase-modulated light L2 at the plurality of focusing positions 91 of the specimen 90. Particularly, in the case of the spatial light modulator using a liquid crystal, such as the LCOS type, the CGH is displayed on the spatial light modulator 20, whereby the spatial light modulator 20 expresses the CGH. That the spatial light modulator 20 expresses the CGH includes that the spatial light modulator 20 presents or displays the CGH. A separate drive unit (not shown) may be provided for performing actual operation so that the control unit 21 controls the drive unit to implement the aforementioned phase modulation and focus. The drive unit in this case sets phase modulation amounts at the respective two-dimensionally arrayed pixels of the spatial light modulator 20 and feeds signals indicative of the phase modulation amounts for the respective pixels to the spatial light modulator 20, under control with the use of the CGH of the control unit 21.

Creation of the CGH may be performed by any technique of the Fourier transform type and the Fresnel zone plate type. The creation of the CGH may be carried out by the control unit 21 or the apparatus may be equipped with a separate CGH creator (not shown). The Fourier transform type can create the hologram by an algorithm such as the GS method, and the Fresnel zone plate type can create the hologram by an algorithm such as the ORA (optimal-rotation-angle) method. The GS method is described in Reference Literature 1 below and the ORA method is described in Reference Literature 2 below.

<Reference Literature 1> R. W. Gerchberg and W. O. Saxton, "A practical algorithm for the determination of phase from image and diffraction plane pictures," Optik, Vol. 35, pp. 237-246 (1972).

<Reference Literature 2> Jorgen Bengtsson, "Kinoform design with an optimal-rotation-angle method," Applied Optics, Vol. 33, No. 29, pp. 6879-6884 (1994).

Figure 2:
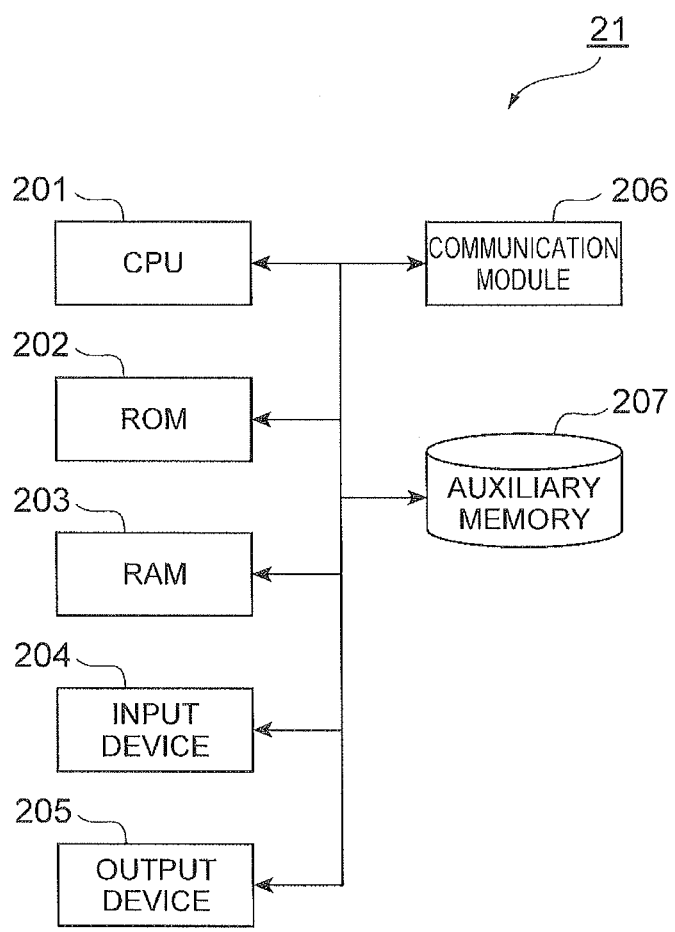
FIG. 2 is a hardware configuration diagram of control unit 21 and correction unit 22.

FIG. 2 is a hardware configuration diagram of the control unit 21. As shown in FIG. 2, the control unit 21 is physically configured as an ordinary computer system including a CPU 201, main storage units such as ROM 202 and RAM 203, an input device 204 such as a keyboard and a mouse, an output device 205 such as a display, a communication module 206 such as a network card for performing transmission/reception of data to or from the spatial light modulator 20 and others, an auxiliary storage unit 207 such as a hard disk, and so on, Each of functions of the control unit 21 is realized by making predetermined computer software read onto hardware such as the CPU 201, ROM 202, and RAM 203, letting the input device 204, output device 205, and communication module 206 operate under control of the CPU 201, and performing readout and writing of data from and into the main storage units 202, 203 and the auxiliary storage unit 207.

Referring back to FIG. 1, the focusing optical system 30 is provided as a subsequent stage to the spatial light modulator 20, and is configured to focus the phase-modulated light L2 resulting from the phase modulation for each pixel, to the specimen 90. In the example of FIG. 1 the focusing optical system 30 is configured with a bi-telecentric lens system 31, a dichroic mirror 32, an objective lens 33, and a lens 34. The phase-modulated light L2 from the spatial light modulator 20 is transferred to the objective lens 33 by the bi-telecentric lens system 31 and dichroic mirror 32 and is applied as multiple spots to the specimen 90 mounted on a specimen stage 92. Fluorescence L3 is generated from the stained specimen 90 by the application of the light, and part of the fluorescence L3 travels via the objective lens 33, dichroic mirror 32, and lens 34 to impinge on a fluorescence receiver 40.

Figure 3:
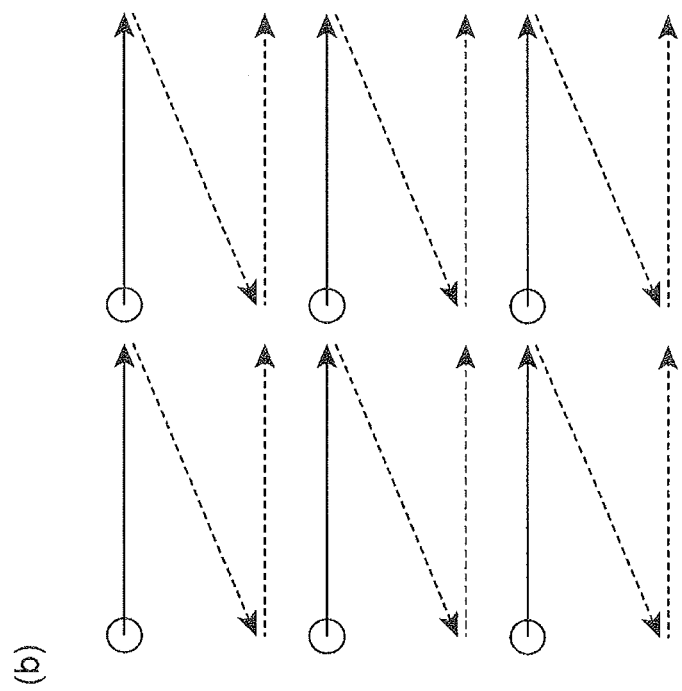
FIG. 3 is a drawing illustrating an example of multi-spot scanning in an embodiment of the invention.
Figure 3:
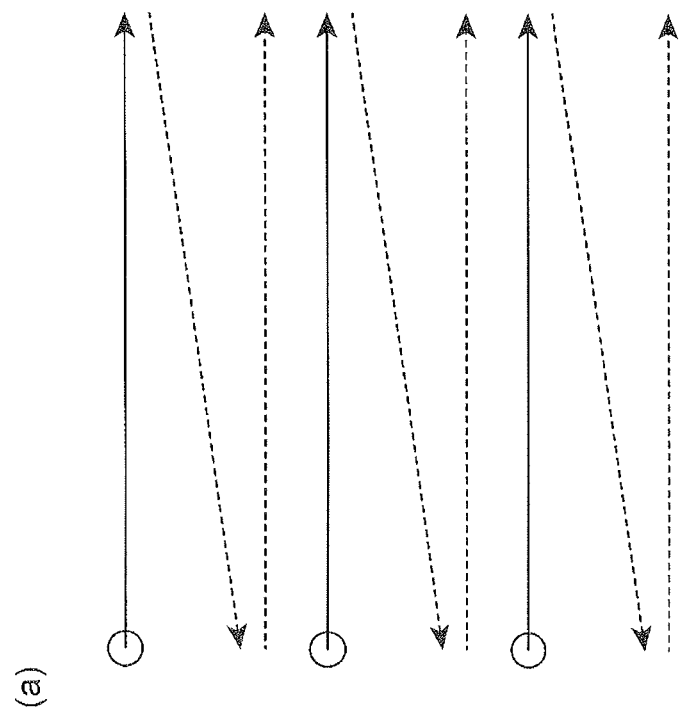

The application of the light to the specimen 90 may be implemented so as to scan the spots with use of a scanner such as a Galvanometer scanner, a resonant mirror, or a polygon mirror and a stage or an objective lens moving in the optical-axis direction, or so as to scan the spots with use of a three-axis stage which moves along a plane perpendicular to the optical axis and along the optical-axis direction. The objective lens 33 in FIG. 1 may be configured to move for scanning. Furthermore, the lens to apply the light to the specimen 90 does not have to be limited to the objective lens but may be a common lens or an Fθ lens. The configuration as described above allows the apparatus to perform multi-spot scanning as exemplified in FIG. 3, thereby enabling high-speed image acquisition. FIG. 3 is a drawing showing examples of the multi-spot scanning in the present embodiment. (a) of FIG. 3 shows the example where multiple spots are one-dimensionally arranged, and (b) of FIG. 3 shows the example where multiple spots are two-dimensionally arranged. In each of the examples, the specimen is scanned with the multiple spots in such a manner that the specimen is first horizontally scanned, then vertically moved by one row, and further scanned (raster scan). It is also possible to adopt various scan techniques with use of multiple spots, as well as the raster scan.

Referring back to FIG. 1, the fluorescence receiver 40 is configured to receive the fluorescence L3 generated by focus of the phase-modulated light L2 to the specimen 90, through the focusing optical system 30 and can be comprised, for example, of a multi-anode type photomultiplier tube (PMT). Without having to be limited to it, the fluorescence receiver 40 to be used herein may be a two-dimensional imaging apparatus such as a photomultiplier tube, CCD, or CMOS image sensor, or a two-dimensional detector such as an avalanche photodiode array or a photodiode array. The fluorescence receiver 40 may be one with location-dependent sensitivity variation specific to the receiver. A pinhole (not shown) may be located in front of the fluorescence receiver 40 so as to achieve the confocal effect.

Figure 4:
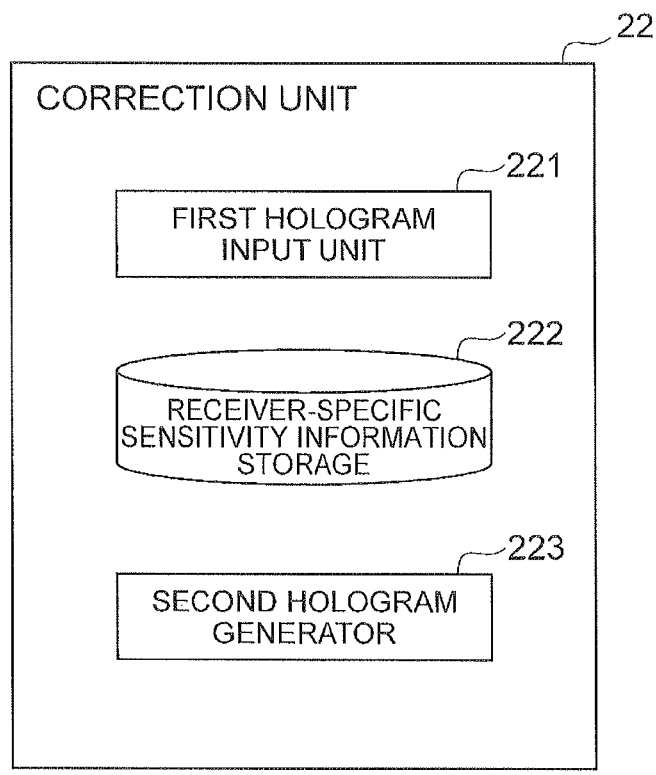
FIG. 4 is a functional configuration diagram of correction unit 22.

The correction unit 22 is a unit that corrects the CGH already presented on the spatial light modulator 20 by the control unit 21. The correction unit 22 has the same hardware configuration as the control unit 21 (cf. FIG. 2). The control unit 21 and the correction unit 22 may exist in the same computer system. FIG. 4 is a functional configuration diagram of the correction unit 22. As shown in FIG. 4, the correction unit 22 is configured with a first hologram input unit 221, a receiver-specific sensitivity information storage 222, and a second hologram generator 223.

The first hologram input unit 221 inputs the CGH already presented on the spatial light modulator 20 by the control unit 21, which is the CGH before correction. The CGH input by the first hologram input unit 221 is a first hologram. The first hologram input unit 221 outputs the input first CGH to the second hologram generator 223.

Figure 5:
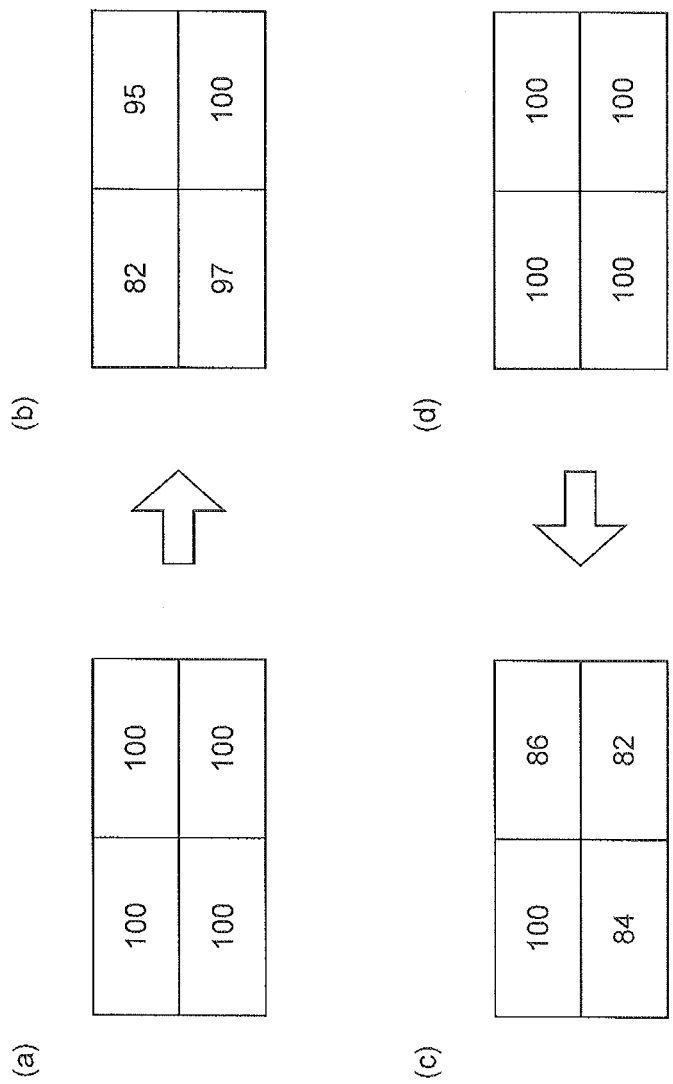
FIG. 5 is a drawing for explaining sensitivity variation per reception position specific to fluorescence receiver 40.

The receiver-specific sensitivity information storage 222 preliminarily acquires and stores sensitivity information per reception position specific to the fluorescence receiver (which will be referred to hereinafter as "receiver-specific sensitivity information"). FIG. 5 is a drawing for explaining the receiver-specific sensitivity information in a two-photon excitation fluorescence microscope. In the example of FIG. 5, there is receiver-specific location-dependent sensitivity variation in the fluorescence receiver 40. Namely, when the fluorescence receiver 40 is, for example, a multi-anode type PMT, there is sensitivity variation among a plurality of anodes. If there is sensitivity variation in uniformity of the anodes with incidence of uniform light independent of locations on a light receiving surface as shown in (a) of FIG. 5, intensity information of the fluorescence detected by the fluorescence receiver 40 will be as shown in (b) of FIG. 5. Namely, even if the fluorescence L3 with uniform intensity of 100 is incident, the fluorescence L3 will be detected with different intensities, e.g., 82, 95, 97, and 100, depending on locations of the fluorescence receiver 40.

Furthermore, even if the fluorescence L3 is detected with uniform intensity by the fluorescence receiver 40 as shown in (d) of FIG. 5, the actually incident fluorescence L3 might be nonuniform as shown in (c) of FIG. 5. Namely, when the fluorescence L3 is detected with uniform intensity, e.g. the intensity of 100, by the fluorescence receiver 40, the spatial light modulator 20 is considered to radiate nonuniform light, for example, with intensities of 100, 86, 84, and 82 in fact. In other words, when the fluorescence L3 is detected with uniform intensity by the fluorescence receiver 40, the incident fluorescence L3 tends to be considered as apparently uniform if no consideration is given to the location-dependent sensitivity variation specific to the fluorescence receiver 40. However, when consideration is given to the location-dependent sensitivity variation specific to the fluorescence receiver 40, the incident fluorescence L3 is determined to be nonuniform in fact.

The receiver-specific sensitivity information storage 222 preliminarily acquires and stores the sensitivity information per reception position specific to the fluorescence receiver 40, with incidence of fluorescence of predetermined uniform intensity. Specifically, the light emitted from the excitation light source 10 is expanded by the expander lens or the like to make parallel light with approximately uniform intensity incident to the fluorescence receiver 40 as a two-dimensional image sensor, and sensitivity unevenness of the fluorescence receiver 40 is investigated in advance. By this investigation, intensities at multiple spots obtained by the fluorescence receiver 40 with incidence of uniform light (fluorescence) are recorded as "receiver-specific sensitivity information." In order to observe the sensitivity variation, a "receiver-specific sensitivity map" may be created as a bundle of pieces of receiver-specific sensitivity information, with a plurality of changes in intensity of light.

The second hologram generator 223 is a unit that performs feedback correction of the first CGH, based on an excitation condition, the intensities of the fluorescence L3 at the focusing positions, and the receiver-specific sensitivity information stored in the receiver-specific sensitivity information storage 222, to generate a second CGH. The second hologram generator 223 outputs the generated second CGH to the control unit 21. The CGH generated by the second hologram generator 223 and output to the control unit 21 is a second hologram. The control unit 21 inputs the second CGH and presents it on the spatial light modulator 20. Namely, the hologram presented on the spatial light modulator 20 by the control unit 21 is subjected to the feedback correction by the correction unit 22 and the hologram after the correction is again presented on the spatial light modulator 20 by the control unit 21. This is repeated until variation of intensities at the multiple spots applied to the specimen 90 becomes not more than a predetermined threshold. Alternatively, it is repeated until the number of times the feedback correction has been executed becomes not less than a predetermined threshold.

(Procedure of Feedback Correction)

Figure 6:
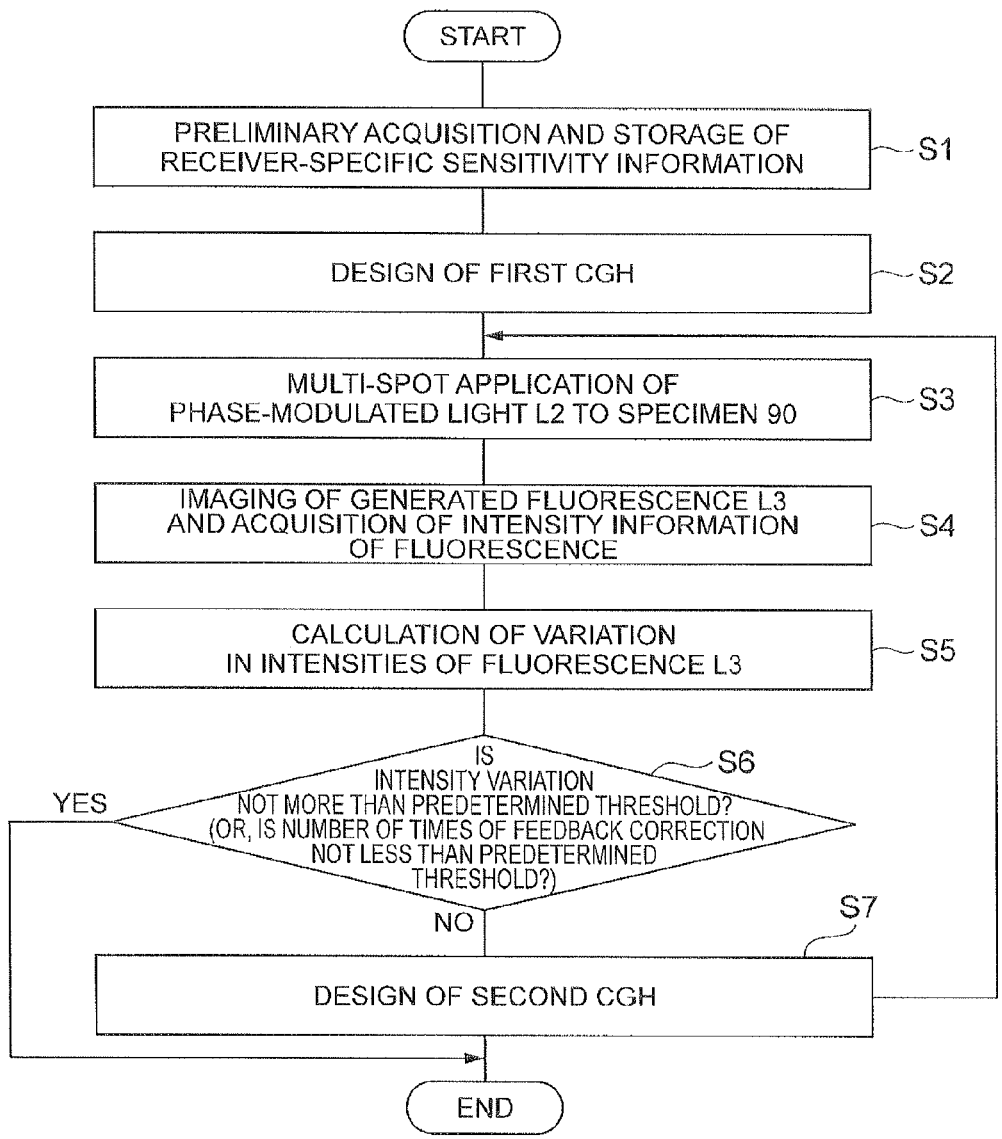
FIG. 6 is a flowchart showing a procedure of feedback correction.

The following will detail the procedure of performing the feedback correction of the first hologram to generate the second hologram. FIG. 6 is a flowchart showing this procedure.

First, the receiver-specific sensitivity information storage 222 preliminarily acquires and stores the receiver-specific sensitivity information with incidence of light with predetermined uniform intensity (step S1).

Next, the first CGH is designed under control of the control unit 21 (step S2).

Next, the first CGH is presented on the spatial light modulator 20 under control of the control unit 21, whereby the spatial light modulator 20 expresses the first CGH. This changes the excitation light L1 into the phase-modulated light L2 with a phase distribution corresponding to the first CGH and this generated phase-modulated light L2 is applied as multiple spots to the specimen 90 (step S3).

Next, the fluorescence receiver 40 images the fluorescence L3 generated by the application in step S3 to acquire intensity information of the fluorescence (step S4).

Next, the correction unit 22 (second hologram generator 223) calculates variation in the intensity information of the fluorescence L3 acquired in step S4. The intensity variation is calculated by the Peak-to-valley (PV) method or by the RMS (Root Mean Square error) method. At this time, the variation of intensities of the fluorescence L3 acquired in step S4 is calculated with consideration to the receiver-specific sensitivity information preliminarily acquired and stored in step S1. For example, if the intensity information of the fluorescence L3 acquired in step S4 is equivalent to the receiver-specific sensitivity information acquired in step S1, the intensity variation can be regarded as zero. When the receiver-specific sensitivity information acquired in step S1 is taken into consideration, it may be further determined whether the result of the evaluation by the Peak-to-valley (PV) method or by the RMS (Root Mean Square error) method is within a certain definite range (step S5).

Next, when the intensity variation calculated in step S5 is not more than the predetermined threshold (step S6: YES), the processing is terminated. On the other hand, when the intensity variation calculated in step S5 is more than the predetermined threshold (step S6: NO), the flow of processing moves to step S7, where, in order to control the fluorescence intensities, the second hologram generator 223 redesigns the first CGH to generate the second CGH. It is assumed in the present embodiment that the fluorescence intensities are to be uniformized, as one mode of the control on the fluorescence intensities. Then, the flow of processing moves to step S3, to repeat step S3 to step S6. For the determination in step S6, it may be determined whether the number of times the feedback correction has been executed is not less than the predetermined threshold, instead of determining whether the intensity variation calculated in step S5 is not more than the predetermined threshold.

(Procedure of Redesign of CGH, No. 1)

The below will describe a method for redesigning the first CGH to generate the second CGH (step S7).

First, the second hologram generator 223 derives correction coefficients Vk to be fed back to the CGH design, by Formula (1) below, based on the intensity variation of the fluorescence L3 acquired in step S4.

[Math 1]

$$v^{(k)}(m) = v^{(k-1)}(m) * \sqrt[2*n]{\frac{q^{(k-1)}(m)}{q^{(k)}(m)}} \quad (1)$$

In this formula, m represents the position of each of the multiple spots, k the number of feedback times, q the intensity of the fluorescence L3 acquired in step S4, and n the number of photons. As seen from the above Formula (1), the correction by the correction unit 22 is carried out for each of the plurality of focusing positions (step S71). In the above Formula (1), the correction coefficients Vk vary depending upon absorption processes of n photons.

Next, the second hologram generator 223 redesigns the first CGH with use of the correction coefficients Vk derived in step S71, to generate the second CGH. For example, in the Over Compensation (OC) method being a kind of iterative Fourier transform, a target pattern (pattern indicative of positions and intensities of the multiple spots) is changed using weights per iteration, and thus the target pattern in the second CGH by the OC method is given by Formula (2) below.

[Math 2]

$$T_I^{(k)}(m) = s(m)v^{(k)}(m)w_I^{(k)}(m)T_{goal}(m) \quad (2)$$

In this formula, "I" represents the number of iterations in the OC method, $$w_I^{(k)}(m) \quad \text{[Math 3]}$$

the weights used in the OC method, $T_{goal}(m)$ the target pattern, and s(m) coefficients with consideration of the receiver-specific sensitivity information (step S72).

(Procedure of Redesign of CGH, No. 2)

The following will describe another method for redesigning the first CGH to generate the second CGH (step S7).

The foregoing CGH redesign procedure No. 1 takes no account of the coefficients s(m) in the correction coefficients Vk and applies the coefficients s(m) to the feedback operation. On the other hand, the CGH redesign procedure No. 2 is different in that the coefficients s(m) are taken into account in the correction coefficients Vk from the beginning.

Namely, first, the second hologram generator 223 derives the correction coefficients Vk to be fed back to the CGH design, by Formula (3) below, based on the intensity variation of the fluorescence L3 acquired in step S4.

[Math 4]

$$v^{(k)}(m) = s(m) * v^{(k-1)}(m) * \sqrt[2*n]{\frac{q^{(k-1)}(m)}{q^{(k)}(m)}} \quad (3)$$

Just as in the case of Formula (1), the correction by the correction unit 22 is also carried out for each of the plurality of focusing positions in the case of Formula (3) being used (step S73).

Next, the second hologram generator 223 redesigns the first CGH with use of the correction coefficients Vk derived in step S73, to generate the second CGH. For example, in the Over Compensation (OC) method being a kind of iterative Fourier transform, a target pattern (pattern indicative of positions and intensities of the multiple spots) is changed using weights per iteration, and thus the target pattern in the second CGH by the OC method is given by Formula (4) below (step S74).

[Math 5]

$$T_l^{(k)}(m) = v^{(k)}(m) w_l^{(k)}(m) T_{goal}(m) \quad (4)$$

(Method for Calculating Coefficients s(m))

The below will describe a method for calculating the coefficients s(m) in a two-photon excitation fluorescence microscope in step S72 and in step S73. It is assumed in the description hereinafter that the receiver-specific sensitivity information acquired in step S1 was, for example, FIG. 5 (*b*).

First, the fourth roots of the receiver-specific sensitivity information acquired in step S1 are calculated. This calculation is attributed to the fact that in the two-photon excitation fluorescence microscope the intensity of the phase-modulated light L2 is the square of the amplitude and the intensity of the fluorescence L3 is the square of the intensity of the phase-modulated light L2. The resultant fourth roots are indicated by Formula (5) below (step S731).

[Math 6]

$$\begin{bmatrix} 3.009 & 3.132 \\ 3.138 & 3.162 \end{bmatrix} \quad (5)$$

Next, each element is divided by the smallest element in Formula (5). The calculation results are indicated by Formula (6) below.

[Math 7]

$$\begin{bmatrix} 1.000 & 1.037 \\ 1.043 & 1.051 \end{bmatrix} \quad (6)$$

Next, the reciprocal of each element in Formula (6) is calculated. The calculation results are indicated by Formula (7) below (step S733).

[Math 8]

$$\begin{bmatrix} 1.000 & 0.964 \\ 0.959 & 0.952 \end{bmatrix} \quad (7)$$

Then, Formula (7) is normalized to obtain the coefficients s(m) in step S72 and in step S73 eventually. The coefficients s(m) calculated are indicated by Formula (8) below (step S734).

[Math 9]

$$\begin{bmatrix} 100 & 96 \\ 96 & 95 \end{bmatrix} \quad (8)$$

When the coefficients s(m) calculated as described above are used in step S72 and in step S73, the CGH redesign procedures No. 1 and No. 2 can be executed.

In the case of an n-photon excitation fluorescence microscope, the above operation is implemented by making use of the fact that the intensity of the phase-modulated light L2 is the square of the amplitude and the intensity of the fluorescence L3 is the n-th power of the intensity of the phase-modulated light L2. For example, in the case of a one-photon excitation fluorescence microscope, the intensity of the phase-modulated light L2 is the square of the amplitude and the intensity of the fluorescence L3 is the first power of the intensity of the phase-modulated light L2; i.e., the intensity of the fluorescence L3 is equal to the intensity of the phase-modulated light L2. For example, in the case of a three-photon excitation fluorescence microscope, the intensity of the phase-modulated light L2 is the square of the amplitude and the intensity of the fluorescence L3 is the third power of the intensity of the phase-modulated light L2.

The intensities of the fluorescence L3, or, q can be derived by a method of calculation to perform the same operation as in the foregoing steps S731 to S734, using the intensity information of the fluorescence L3 acquired in step S4 by the fluorescence receiver 40, instead of the receiver-specific sensitivity information (e.g., (b) of FIG. 5).

By executing step S1 to step S7 described above, it is feasible to control both of the phase-modulated light L2 applied to the specimen 90 and the fluorescence L3 emitted from the specimen 90, for example, to uniform intensity levels. Here, for uniformizing each of the phase-modulated light L2 applied to the specimen 90 and the fluorescence L3 emitted from the specimen 90, the specimen 90 to be used may be such a homogeneous fluorescent material that fluorescence is emitted with the same intensity, irrespective of positions of irradiation, as long as the intensity of the excitation light is the same. Namely, a homogeneous fluorescent material without location-dependent variation in a ratio of intensities of the fluorescence L3 generated from the specimen 90 to the phase-modulated light L2 focused to the specimen 90 may be used as the specimen 90 in the present embodiment.

The shading correction by image processing or the like may be further applied, in order to uniformize the location-dependent sensitivity variation per reception position specific to the fluorescence receiver 40. This can reduce the number of times the feedback correction is to be executed.

The design methods hereinbefore were described according to the OC method, but the CGH design methods do not have to be limited to the OC method. The CGH design methods that can be adopted herein include the iterative Fourier transform methods including the OC method, methods with focus on change of one pixel such as the simulated annealing, Optimal rotation angle method (ORA method), and genetic algorithm, and the superposition method to implement superposition in the form of complex amplitude.

Any one of the above-listed techniques also uses the above Formula (1) or Formula (3) in the feedback operation.

(Z-Stack)

The correction by the correction unit 22 described above may be performed for each of scanned layers at predetermined intervals along the optical-axis direction of the objective lens 33 included in the focusing optical system 30. The below will describe z-stack for realizing the correction per scanned layer. The z-stack refers to acquisition of a three-dimensional image by taking images of the specimen 90 with shifts in the depth direction. The z-stack is implemented with movement of the scanned layers at the predetermined intervals along the optical-axis direction of the objective lens 33 by (a) a method for presenting a Fresnel lens pattern on the spatial light modulator 20, (b) a method for moving a Z-stage of the fluorescence scanning microscope apparatus including the fluorescence receiving apparatus 1, (c) a method for moving the objective lens 33 itself, or (d) a combination of these methods.

The below will describe a processing procedure for performing the z-stack. The following will describe an example of performing the scan by performing the control in the depth direction along the optical-axis direction of the objective lens 33 by adding a Fresnel lens to the CGH for generation of multiple spots presented on the spatial light modulator 20, i.e., by the above method (a), and by moving the scanned layers in three depths D1, D2, and D3.

First, the CGH for generation of multiple spots is designed (step S101).

Next, a Fresnel lens for observation in the depth D1 is added to the CGH designed in step S101 (step S102).

Next, an aberration correction pattern is further added to the CGH synthesized in step S102 as occasion demands (step S103).

Next, the CGH synthesized in step S103 is presented on the spatial light modulator 20, whereby the spatial light modulator 20 expresses the CGH synthesized in step S103, to apply generated multiple spots onto a homogeneous specimen 90 (step S104).

Next, a fluorescence image generated from the specimen 90 is taken with a multi-anode type PMT, camera, or the like (step S105).

Next, variation of detected fluorescence intensities is inspected. The Peak-to-valley (PV) method or the RMS (Root Mean Square error) method is used for calculation of the variation. At this time, the variation may be checked among total intensities each of which is determined in such a manner that an observation region is set as a region centered on a center of each focused spot and a total of intensities is calculated in each observation region. When the specimen is observed with addition of intentionally large aberration to perform aberration correction taking account of a living body, the observation region may be set so as to cover an entire spot broadened by the aberration. The "intentionally large aberration" herein refers, for example, to aberration in the range of not less than "n×d−Δs" and not more than "n×d+Δs" where n is the refractive index of the medium, d the depth from a plane of incidence to the medium to the focal point of the lens, and Δs the aberration generated by the medium. Without having to be limited to this, the foregoing "intentionally large aberration" may be set as follows: spherical aberration produced due to mismatching of the refractive, index of the observation object with that of an immersion liquid or the like, astigmatism produced by the shape of the object, or other aberration is preliminarily measured by simulation or by use of a Shack-Hartman sensor or the like, and the aberration in a range taking further account of these is defined as the foregoing "intentionally large aberration" (step S106).

The processing is terminated if the variation calculated in step S106 is within a permissible range (step S107).

If the variation calculated in step S106 is out of the permissible range, redesign of CGH is performed using the CGH designed in step S101 as an initial phase. Namely, the CGH designed in step S101 is used as the first CGH to generate the second CGH by use of the aforementioned CGH redesign procedures No. 1 and No. 2 and the calculation method of the coefficients s(m) (step S108).

Next, with repetitions of step S104 to step S108, the iterative operation is continued until the variation calculated in step S106 becomes within the permissible range; whereby an optimal CGH for the depth D1 is designed. In this iterative operation, step S102 and step S103 are excluded. Namely, the procedure of step S102 and step S103 is carried out only once for each depth (step S109).

Next, the depth is changed to D2 and then the processing of step S101 to step S109 is carried out. Furthermore, the depth is changed to D3 and then the processing of step S101 to step S109 is carried out.

Finally, the CGHs optimized for the respective depths are presented at the respective depths to perform the scan in the z-stack.

In the above description, the case of the aforementioned method (a) was explained as the method for performing the z-stack. Namely, the above described the case where the spatial light modulator 20 controlled the focusing positions in the optical-axis direction of the objective lens 33, thereby performing the scanning for each scanned layer. Without having to be limited to this, the same procedure as above can also be applied to the cases of the foregoing methods (b) and (c). The change of depth was implemented by changing the Fresnel lens patterns in the method (a), whereas the change of depth is implemented by moving the Z-stage in the case of the method (b) and by moving the objective lens 33 in the case of the method (c).

Since the fluorescence intensities are not uniform because of the characteristics of the spatial light modulator 20, adjustment error of the focusing optical system 30, etc., the present embodiment involves execution of the feedback correction to design the CGH corrected for these problems and re-presentation thereof on the spatial light modulator 20. However, if the Z-axis is moved for performing the z-stack, the optical system will vary due to optical variation in the state of the medium in a focusing process and thus it might destroy the uniformity of fluorescence intensities controlled by the feedback correction with effort. Furthermore, when the z-stack is realized by use of the Fresnel lens patterns, the addition of the Fresnel lens patterns can cause the optimum CGH determined with effort to become no longer the optimum CGH. When the object is observed through the objective lens with high NA or the like, various media with different refractive indices exist between the objective lens and the object and they produce aberration. It can be contemplated that an aberration correction pattern is presented on the spatial light modulator 20 to correct the aberration, but it results in again changing the condition for achievement of the optimum CGH.

In order to handle the above-described problem, the present embodiment is configured to add the Fresnel lens pattern and the aberration correction pattern to the first designed CGH and not to use the Fresnel lens pattern and the aberration correction pattern for the feedback correction. By this, the aberration is corrected by the aberration correction pattern and, after the Fresnel lens pattern and the aberration correction pattern are fixed, the feedback correction is performed. Therefore, even if the addition of the Fresnel lens pattern or the like causes movement of the Z-axis so as to result in change in the optical state of the medium and in the optical system or even if aberration is produced because of the optical system such as the high-NA objective lens or the difference of refractive index in the medium existing in the propagation process, the aberration can be corrected and the uniformity of fluorescence intensities achieved by the feedback correction can be maintained.

In the fluorescence receiving apparatus 1 of the present embodiment, the first CGH first expressed by the spatial light modulator 20 is corrected by the correction unit 22 and the second CGH newly generated by the correction is again expressed by the spatial light modulator 20. Namely, the hologram is fed back by the correction unit 22 and the control unit 21, thereby performing the correction of the hologram. The second CGH is obtained by the correction of the first CGH, based on the excitation condition, the intensities of the fluorescence L3 at the focusing positions, and the receiver-specific sensitivity information, and this second CGH controls the intensity variation at the multiple spots generated by the spatial light modulator 20, for example, to a uniform intensity level, while taking account of the sensitivity variation in the fluorescence receiver 40. Here, the feedback correction of the hologram results in controlling each of the phase-modulated light L2 applied to the specimen 90 and the fluorescence L3 emitted from the specimen 90, for example, to a uniform intensity level. Particularly, since the correction by the correction unit 22 is performed based on the receiver-specific sensitivity information, the location-dependent sensitivity variation per reception position specific to the fluorescence receiver 40 is admitted, but influence of the sensitivity variation can be reduced.

Figure 7:
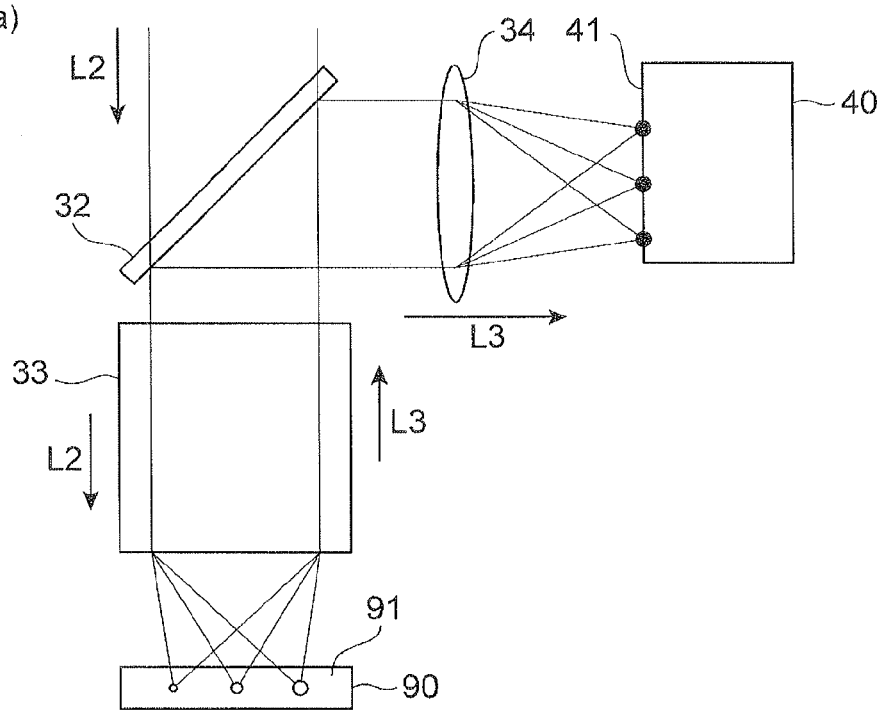
FIG. 7 is a drawing for explaining the embodiment of the invention wherein the correction unit 22 performs feedback correction based on sensitivity information per reception position specific to the fluorescence receiver 40, whereby, while admitting location-dependent sensitivity variation per reception position specific to the fluorescence receiver 40, influence of the sensitivity variation is reduced and intensities of phase-modulated light L2 and fluorescence L3 are made uniform.
Figure 7:
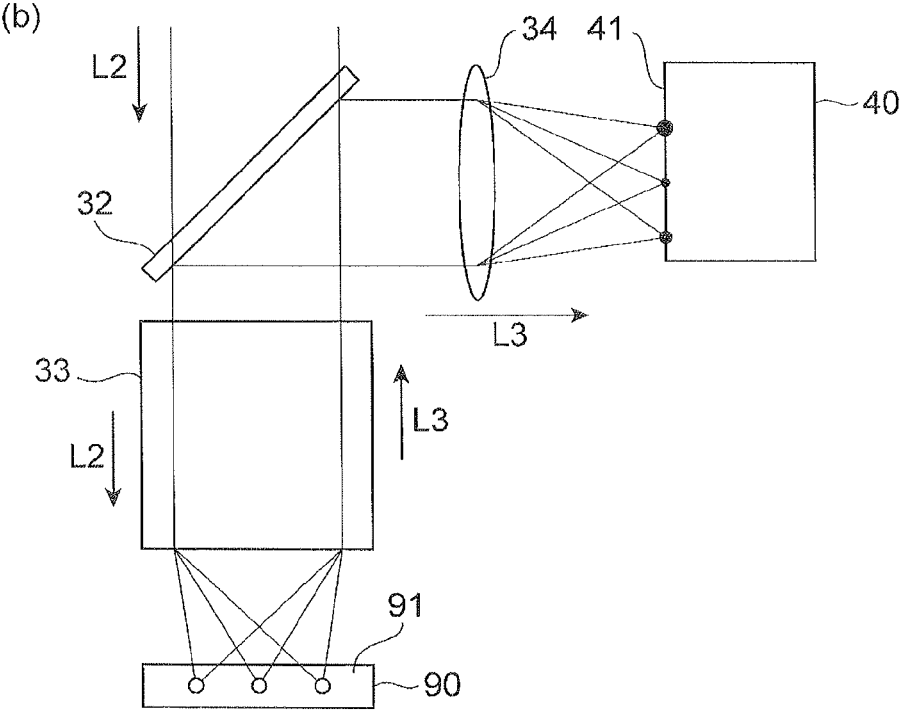

FIG. 7 is a drawing for explaining other aspects of the concept of the present embodiment. (a) of FIG. 7 images the situation, as described above using (a) and (b) of FIG. 5, wherein, although the incident fluorescence L3 tends to be considered as apparently uniform, the incident fluorescence L3 is nonuniform in fact, with consideration of the location-dependent sensitivity variation specific to the fluorescence receiver 40. In (a) of FIG. 7, levels of intensity are indicated by sizes of dots at the focusing positions 91 of the specimen 90 and at reception positions 41 on the fluorescence receiver 40. Namely, the sizes of dots are different at the focusing positions 91 of the specimen 90, which indicates that the intensities of light at the focusing positions are nonuniform. On the other hand, the sizes of dots are equal at the reception positions 41 on the fluorescence receiver 40, which indicates that the intensities of light at the reception positions 41 appear uniform.

On the other hand, (b) of FIG. 7 images the situation, as described above using (c) and (d) of FIG. 5, wherein, although the intensities of the fluorescence detected by the fluorescence receiver 40 are nonuniform, the intensities of the phase-modulated light L2 incident to the specimen 90 and the fluorescence 13 are uniform. This means that the correction unit 22 in the present embodiment performs the feedback correction based on the receiver-specific sensitivity information whereby, while admitting the location-dependent sensitivity variation per reception position specific to the fluorescence receiver 40, the influence of the sensitivity variation is reduced, so as to uniformize the intensities of the phase-modulated light L2 and the fluorescence L3.

Figure 8:
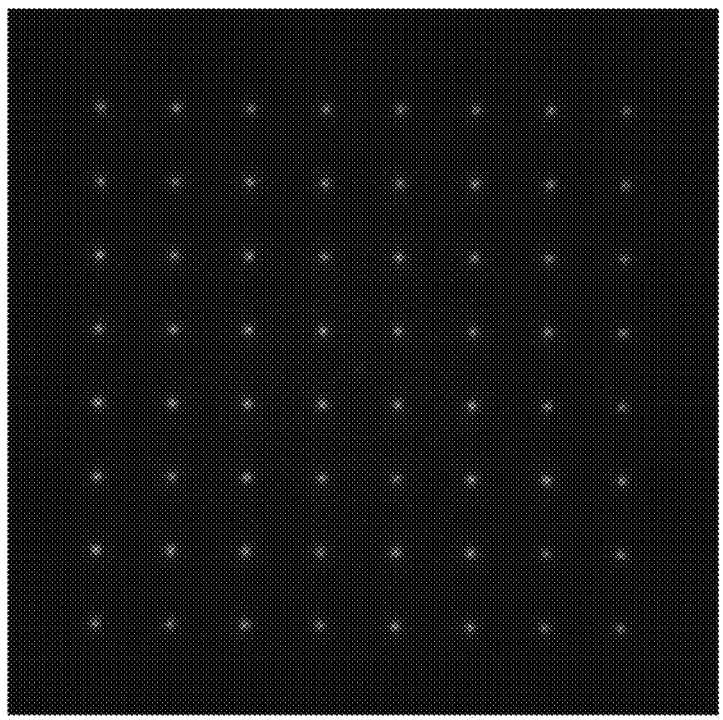
FIG. 8 is a drawing for explaining effects by the embodiment of the invention.
Figure 8:
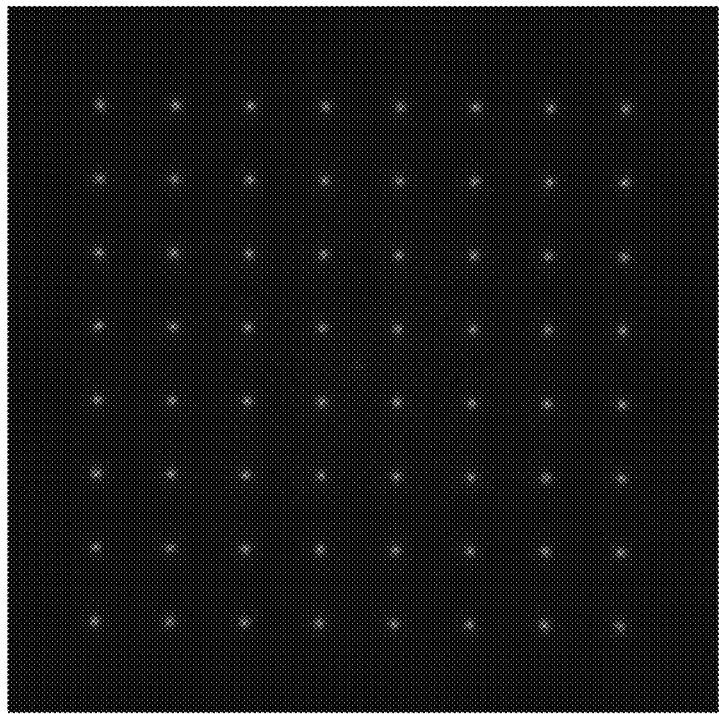

The effects by the present embodiment will be described with an actual example. Namely, in this actual example the specimen 90 used was an rAcGFP1 solution and multi-spot irradiation was carried out by the fluorescence receiving apparatus 1. The result thereof is shown in FIG. 8. (a) of FIG. 8 shows a fluorescence image before execution of the feedback correction. In (a) of FIG. 8 the fluorescence intensities are lower in the upper right region than in the central region and there is also location-dependent intensity variation near the center though it is difficult to identify it by visual observation. In FIG. 8, intensities of fluorescence are indicated by brightness levels. (b) of FIG. 8 shows a fluorescence image after execution of the feedback correction according to the present embodiment. It is seen that the location-dependent sensitivity variation is reduced, different from (a) of FIG. 8. FIG. 8 shows the intensities of the fluorescence detected at the respective reception positions, with consideration of the receiver-specific sensitivity information.

FIG. 9 is a drawing showing a relationship between the number of times the feedback correction has been executed according to the present embodiment (on the horizontal axis) and variation of fluorescence intensities (on the vertical axis). Evaluation functions for the variation used were the Peak-to-valley (PV) method and RMS (Root Mean Square error) method as described above. The calculated variations in the PV method and in the RMS method can be expressed by Formulas (9) and (10) below, respectively.

[Math 10]
$$PV = \frac{(q_{max} - q_{min})}{2 * q_{desired}} \quad (9)$$

[Math 11]
$$RMS = \sum_{m=1}^{M} \sqrt{\frac{[q(m) - q_{desired}]^2}{M}} \quad (10)$$

In the above formulas, q(m) represents the sum of fluorescence in the m-th fluorescence observation region, and qmax, qmin, and qdesired the maximum, minimum, and desired fluorescence intensities, respectively. As shown in FIG. 9, PV=26% and RMS=10% before the correction (the number of times the feedback correction has been executed=0), whereas PV=3% and RMS=1%, confirming significant improvement after the feedback correction was performed six times.

In the present embodiment, the fluorescence L3 is detected with the specimen 90 being placed. Advantages of the detection of fluorescence with the specimen 90 being placed are as described below. Namely, after the correction is performed once using as the specimen 90 a medium with which the fluorescence is obtained with uniform intensity, such as the rACGFP solution or coumarin ethanol, uniform data is obtained even with use of cells or the like as a specimen, which is the first advantage. The second advantage is that the use of the specimen allows the optical system actually used for measurement to be used, enabling the correction of the entire optical system. The third advantage is that, by preparing a homogeneous medium with the refractive index close to an observation condition, uniformity can be achieved with the spherical aberration correction and lens pattern being applied. If there is an extreme difference between the refractive indices of the specimen 90 and the observation medium, the focused image will be blurred to reduce SN, causing a risk of degrading the accuracy of uniformity. Therefore, the refractive index of the specimen 90 may be matched with the refractive index of the observation medium to some extent. Furthermore, the OC method is an optimization approach, in which a random phase is often used as an initial phase, in order to prevent convergence to a local solution. As a result, a distribution of variation of generated multiple spots differs every first hologram. Or, even if an identical initial phase is used, the distribution of variation of multiple spots generated by the first hologram will differ with change in positions and intensities of multiple spots in the target pattern. The fourth advantage is that the hologram-originating variation can be precisely grasped by use of the medium to ensure uniform fluorescence intensity, as the specimen 90.

Since the present embodiment is configured to perform the correction by the correction unit 22 for each of the plurality of focusing positions, the correction can be applied to each of the multiple spots generated by the spatial light modulator 20 and hologram.

This invention is particularly useful to the intensity variation at the plurality of focusing positions, which occurs in the case where a short pulsed laser capable of inducing multiphoton excitation is used as the excitation light source 10. A preferred example of such excitation light source 10 is a light source capable of emitting a short pulsed laser having the wavelength of not less than 650 nm.

The present embodiment is particularly useful to the fluorescence receiver 40 with the location-dependent sensitivity variation, such as the multi-anode type photomultiplier tube.

The present embodiment allows the homogeneous fluorescent material without location-dependent variation to be used as the specimen 90 in controlling both of the phase-modulated light L2 to the specimen 90 and the fluorescence L3 from the specimen 90, for example, to uniform intensity levels, whereby it can reduce computational complexity and readily and suitably perform the control.

Since the present embodiment is configured to perform the correction by the correction unit 22 for each of the scanned layers at the predetermined intervals along the optical-axis direction of the objective lens 33 included in the focusing optical system 30, the present embodiment can also be applied to the specimen 90 with some depth.

Since the present embodiment is configured to perform the scan for each scanned layer so that the spatial light modulator 20 controls the focusing positions in the optical-axis direction of the objective lens 33, it can suitably perform the scan for each scanned layer.

The specimen to be used may be a calibration specimen with a uniform concentration of a solute such as a fluorescent substance, having the refractive index close to that of an actually measured specimen. By using such a calibration specimen, the uniformity of fluorescence intensities can be ensured.

INDUSTRIAL APPLICABILITY

The present invention provides the fluorescence receiving apparatus and fluorescence receiving method enabling the control of the intensities of the multiple spots of fluorescence at the focusing positions.

The invention claimed is:
1. An apparatus for receiving fluorescence generated from a specimen by focus of phase-modulated excitation light, comprising:
light source configured to output an excitation light;
a spatial light modulator of a phase modulation type configured to input the excitation light, modulate phase of the excitation light and output the phase-modulated light;
a focusing optical system configured to input the phase-modulated light and focus the phase-modulated light to the specimen;
a stage configured to support the specimen;
a light detector configured to detect fluorescence generated by the phase-modulated light, via the focusing optical system;
a controller configured to control the spatial light modulator so as to display a first hologram to modulate a phase of the excitation light at each of a plurality of two-dimensionally arrayed pixels, thereby focusing the phase-modulated light at a plurality of focusing positions of the specimen by the focusing optical system; and
a correction unit configured to correct the first hologram based on intensities of the fluorescence at the focusing positions and sensitivity information per reception position specific to the light detector, to generate a second hologram and,
wherein the controller controls the spatial light modulator so as to display the second hologram.

2. The apparatus according to claim 1, wherein the correction by the correction unit is performed for each of the plurality of focusing positions.

3. The apparatus according to claim 1, wherein the light source outputs a short pulsed laser capable of inducing multiphoton excitation.

4. The apparatus according to claim 1, wherein the light detector is a multi-anode type photomultiplier tube.

5. The apparatus according to claim 1, wherein the specimen is comprised of a homogeneous fluorescent material without location-dependent variation in a ratio of intensities of the fluorescence generated from the specimen to the phase-modulated light focused to the specimen.

6. The apparatus according to claim 1, wherein the correction by the correction unit is performed for each of scanned layers at predetermined intervals along an optical-axis direction of an objective lens included in the focusing optical system.

7. The apparatus according to claim 6, wherein scanning for each of the scanned layers is performed in such a manner that the spatial light modulator controls the focusing positions in the optical-axis direction of the objective lens.

8. A method for receiving fluorescence generated from a specimen mounted on a stage by focus of phase-modulated excitation light, comprising:
outputting an excitation light;
modulating phase of the excitation light by a spatial light modulator of a phase modulation type and outputtings phase-modulated light;
focusing the phase-modulated light to the specimen by a focusing optical system;
detecting fluorescence generated by the phase-modulated light, via the focusing optical system, using a light detector;
controlling the spatial light modulator so as to display a first hologram to modulate a phase of the excitation light at each of a plurality of two-dimensionally arrayed pixels, thereby focusing the phase-modulated light at a plurality of focusing positions of the specimen by the focusing optical system;
correcting the first hologram based on intensities of the fluorescence at the focusing positions and sensitivity information per reception position specific to the light detector, to generate a second hologram;
controlling the spatial light modulator so as to display the second hologram.

* * * * *